United States Patent
Spangler et al.

(10) Patent No.: US 11,090,079 B2
(45) Date of Patent: Aug. 17, 2021

(54) ATHERECTOMY MOTOR CONTROL SYSTEM WITH HAPTIC FEEDBACK

(71) Applicant: BOSTON SCIENTIFIC SCIMED, INC., Maple Grove, MN (US)

(72) Inventors: David Gordon Spangler, New Richmond, WI (US); Daniel Frank Massimini, Brooklyn Park, MN (US); Laszlo Trent Farago, Hudson, WI (US); Corydon Carlson, Stillwater, MN (US); Mark A. Hilse, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 239 days.

(21) Appl. No.: 16/287,689

(22) Filed: Feb. 27, 2019

(65) Prior Publication Data
US 2019/0262034 A1   Aug. 29, 2019

Related U.S. Application Data

(60) Provisional application No. 62/636,120, filed on Feb. 27, 2018.

(51) Int. Cl.
*A61B 17/3207* (2006.01)
*G05B 11/42* (2006.01)
(Continued)

(52) U.S. Cl.
CPC ...... *A61B 17/320758* (2013.01); *A61B 34/76* (2016.02); *G05B 11/42* (2013.01);
(Continued)

(58) Field of Classification Search
CPC ............ A61B 17/320758; A61B 34/76; A61B 2017/00022; A61B 2017/00402;
(Continued)

(56) References Cited

U.S. PATENT DOCUMENTS 5,287,858 A  *   2/1994  Hammerslag .. A61B 17/320758
                                                            600/585
8,603,123 B2 * 12/2013  Todd ................ A61B 17/32002
                                                            606/167
(Continued)

FOREIGN PATENT DOCUMENTS

EP          3053534 A1     8/2013

OTHER PUBLICATIONS

International Search Report and Written Opinion dated Apr. 26, 2019, for International Application No. PCT/US2019019848.

*Primary Examiner* — Julian W Woo
(74) *Attorney, Agent, or Firm* — Seager, Tufte & Wickhem, LLP

(57) ABSTRACT

An atherectomy system includes a drive mechanism adapted to rotatably actuate an atherectomy burr and a control system that is adapted to regulate operation of the drive mechanism. The drive mechanism may include a drive cable that is coupled with the atherectomy burr and a drive motor that is adapted to rotate the drive cable. The control system includes a drive module adapted to provide an operational signal to operate the drive mechanism, a monitoring module adapted to monitor operation of the drive mechanism and to determine if the drive mechanism is operating within a predetermined range and an excitation module that is operably coupled to the drive mechanism and is adapted to provide haptic feedback to a user of the drive mechanism if the monitoring module determines that the drive mechanism is not operating within a predetermined range.

19 Claims, 6 Drawing Sheets

(51) Int. Cl.
*A61B 34/00* (2016.01)
*A61B 17/00* (2006.01)
*A61B 90/00* (2016.01)
*A61B 18/00* (2006.01)

(52) U.S. Cl.
CPC ........... *A61B 2017/00017* (2013.01); *A61B 2017/00022* (2013.01); *A61B 2017/00119* (2013.01); *A61B 2017/00132* (2013.01); *A61B 2017/00199* (2013.01); *A61B 2017/00398* (2013.01); *A61B 2017/00402* (2013.01); *A61B 2018/00303* (2013.01); *A61B 2090/066* (2016.02); *A61B 2090/08021* (2016.02); *A61B 2217/005* (2013.01); *A61B 2217/007* (2013.01); *A61M 2205/582* (2013.01)

(58) Field of Classification Search
CPC .... A61B 2017/00199; A61B 2090/066; A61B 2017/00132; A61B 2217/007; A61B 2217/005; A61B 2017/00119; A61B 2090/08021; A61B 2018/00303; A61B 2017/00398; A61B 2017/00017; G05B 11/42; A61M 2205/582
See application file for complete search history.

(56) References Cited

U.S. PATENT DOCUMENTS

| | | | |
|---|---|---|---|
| 9,050,126 B2 * | 6/2015 | Rivers | A61B 17/320758 |
| 2011/0251554 A1 | 10/2011 | Romoscanu | |
| 2020/0022764 A1 * | 1/2020 | Flexman | A61B 5/065 |

* cited by examiner

ATHERECTOMY MOTOR CONTROL SYSTEM WITH HAPTIC FEEDBACK

CROSS-REFERENCE TO RELATED APPLICATIONS

This application claims the benefit of priority under 35 U.S.C. § 119 of U.S. Provisional Application No. 62/636,120, filed Feb. 27, 2018, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, the disclosure is directed to an atherectomy device system that includes a drive mechanism adapted to rotatably actuate an atherectomy burr and a control system that is adapted to regulate operation of the drive mechanism. The control system includes a drive module that is adapted to provide an operational signal to operate the drive mechanism, a monitoring module that is adapted to monitor operation of the drive mechanism and to determine if the drive mechanism is operating within a predetermined range and an excitation module that is operably coupled to the drive mechanism and is adapted to provide haptic feedback to a user of the drive mechanism if the monitoring module determines that the drive mechanism is not operating within a predetermined range.

Alternatively or additionally, the drive mechanism may include a drive cable that is coupled with the atherectomy burr and a drive motor that is adapted to rotate the drive cable.

Alternatively or additionally, the monitoring module may be adapted to determine if the drive mechanism is operating within a predefined speed range.

Alternatively or additionally, the monitoring module may be adapted to determine if the drive mechanism is operating within a predefined torque range.

Alternatively or additionally, the monitoring module may be adapted to determine if the drive mechanism is operating within a predefined run time range.

Alternatively or additionally, the drive mechanism may further include a handle with the drive cable extending through the handle, and the excitation module, when actuated, causes a detectable vibration within the handle.

Alternatively or additionally, the excitation module may include a vibrator motor that, when actuated, causes a detectable vibration within the drive mechanism.

Alternatively or additionally, when the monitoring module determines that the drive mechanism is operating outside the predetermined range by a preset amount, the excitation module may be further adapted to increase the haptic feedback.

Another example of the disclosure is an atherectomy system that includes a handle and a drive motor that is adapted to rotate a drive cable extending through the handle and is operably coupled to an atherectomy burr. An excitation module is operably coupled to the handle and is adapted to provide haptic feedback to a user of the atherectomy system. A monitoring system is adapted to monitor operation of the drive motor and is further adapted to monitor a motor performance parameter and when the motor performance parameter approaches a predetermined value for the motor performance parameter, actuate the excitation module in order to provide haptic feedback to the user of the atherectomy system that the motor performance parameter is approaching the predetermined value for the motor performance parameter.

Alternatively or additionally, the atherectomy system may further include a control system adapted to control operation of the drive motor.

Alternatively or additionally, the monitoring system may be integrated into the control system.

Alternatively or additionally, the motor performance parameter may include a motor speed.

Alternatively or additionally, the motor performance parameter may include a motor torque.

Alternatively or additionally, the motor performance parameter may include an elapsed run time.

Alternatively or additionally, the haptic feedback may include a detectable vibration.

Another example of the disclosure is a control system for an atherectomy system that includes a drive motor adapted to rotate a drive cable operably coupled to an atherectomy burr. The control system includes an input that is adapted to receive an indication of a motor performance parameter and an excitation module adapted to provide haptic feedback to a user of the atherectomy system. A controller is operably coupled to the input and to the excitation module and is adapted, when the motor performance parameter approaches a limit of a performance range, to activate the excitation module in order to provide haptic feedback to the user that the motor performance parameter is approaching the limit of the performance range.

Alternatively or additionally, the controller may be further adapted to output control signals for operation of the drive motor.

Alternatively or additionally, the motor performance parameter may include a motor speed.

Alternatively or additionally, the motor performance parameter may include a motor torque.

Alternatively or additionally, the motor performance parameter may include an elapsed run time.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
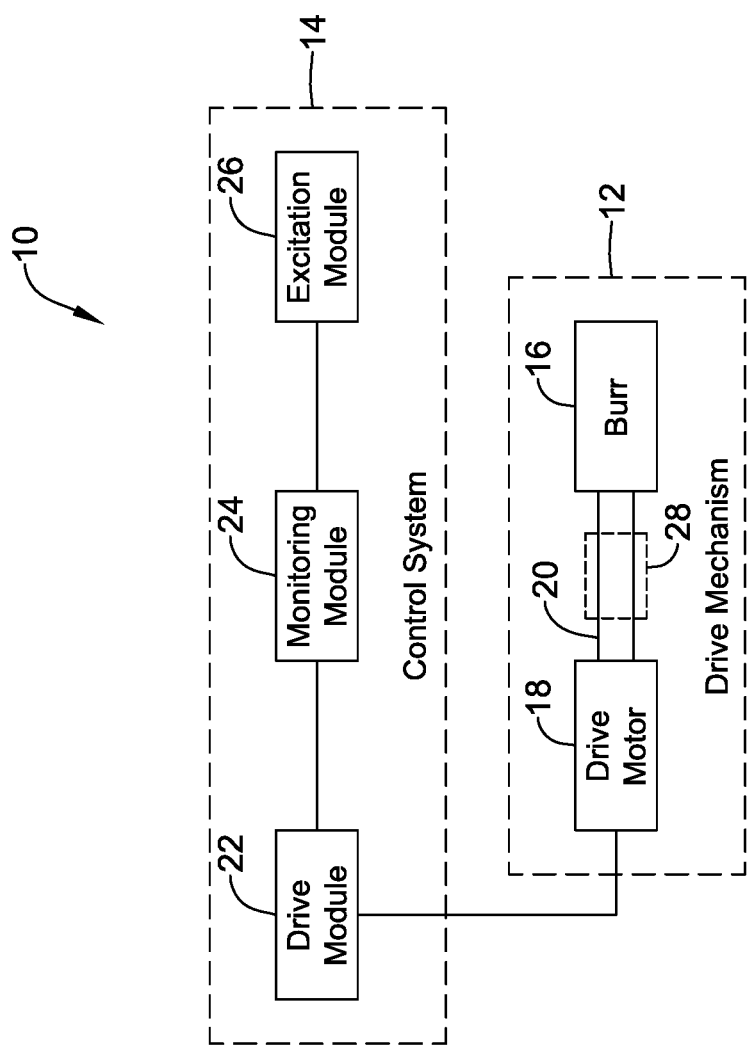
FIG. 1 is a schematic block diagram of an example atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 is a schematic block diagram of an example atherectomy system 10. In some cases, the atherectomy system 10 may be considered as including a drive mechanism 12 and a control system 14. The drive mechanism 12 is adapted to rotatably actuate an atherectomy burr 16 and in some cases includes a drive motor 18 that is adapted to rotatably engage a drive cable 20. As the drive motor 18 causes the drive cable 20 to rotate, the atherectomy burr 16 is also driven into rotation. In some cases, the atherectomy burr 16 may also be referred to as being or including a cutting head or a cutting member, and these terms may be used interchangeably. The control system 14 may be adapted to regulate operation of the drive mechanism 12, and the control system 14 may include a drive module 22 that is adapted to provide an operational signal to operate the drive mechanism 12. The control system 14 includes a monitoring module 24 that is adapted to monitor operation of the drive mechanism 12, and to determine when and/or if the drive mechanism 12 is operating within a predetermined range. In some cases, the atherectomy system 10 may include additional components not illustrated, such as but not limited to suction or vacuum systems, fluid sources, and the like.

In some cases, the monitoring module 24 is adapted to determine if the drive mechanism 12 is operating within a predefined speed range. In some cases, the monitoring module 24 is adapted to determine if the drive mechanism 12 is operating within a predefined torque range. The monitoring module 24 may be adapted to determine if the drive mechanism 12 is operating within a predefined run time range. In some cases, the monitoring module 24 may monitor a plurality of different operating parameters, including speed, torque and elapsed time, as well as other possible operating parameters such as but not limited to saline pressure and axial force being applied to the burr 16. An excitation module 26 is operably coupled to the drive mechanism 12 and is adapted to provide haptic feedback to a user of the drive mechanism 12 if the monitoring module 24 determines that the drive mechanism 12 is not operating within a predetermined range. In some cases, the speed may vary from 0 to about 250,000 rpm, the torque range may vary from 0 to about 5 inch-ounces and the run time range may vary from 0 to about 30 minutes. It will be appreciated that narrower ranges within these given ranges may be contemplated. In some cases, these parameters may be useful in ascertaining of the drive mechanism 12 is operating properly and efficiently, or if the atherectomy burr 16 is encountering excessive resistance, for example.

In some cases, if the monitoring module 24 determines that the drive mechanism 12 is operating outside the predetermined range by at least a preset amount, the excitation module 26 may be further adapted to increase the haptic feedback. For example, if the current motor speed is more than ten percent, or more than twenty percent over the predetermined range; or if the current motor torque is more than ten percent, or more than twenty percent over the predetermined range; or if the current run time exceeds the predetermined run time range by more than ten percent or more than twenty percent. In some cases, the haptic feedback may proportionally increase as the parameter in question (such as speed or torque) continues to move farther and farther away from a predetermined range.

In some cases, the drive mechanism 12 may further include a handle 28, shown in dashed line in FIG. 1, with the drive cable 20 extending through the handle 28. The excitation module 26 may be positioned and/or adapted to cause a detectable vibration within the handle 28 when the excitation module 26 is activated. In some cases, the excitation module 26 may be a vibration motor. In some cases, the excitation module 26 may be a piezoelectric element that is adapted to cause a vibration when electrical power is applied to the piezoelectric element, or any other device capable of inducing vibratory feedback.

Figure 2:
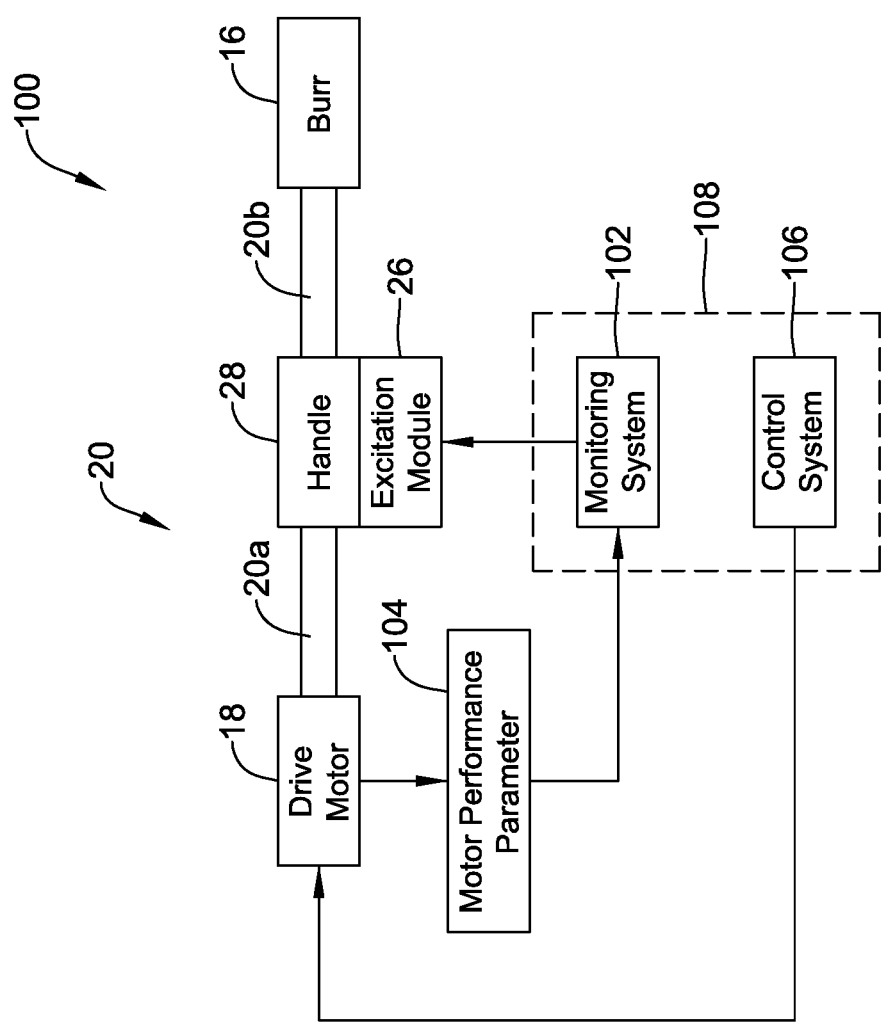
FIG. 2 is a schematic block diagram of an example atherectomy system.

FIG. 2 is a schematic block diagram of an example atherectomy system 100. It will be appreciated that features of the atherectomy system 10 may be included in the atherectomy system 100, and vice versa. As can be seen, the drive cable 20 extends from the drive motor 18 and through the handle 28, such that the drive cable 20 may be considered as including a first section 20a that is proximal to the handle 28, and adjacent the drive motor 18, and a second section 20b that is distal to the handle 28, and adjacent the atherectomy burr 16.

The atherectomy system 100 includes a monitoring system 102 and in some cases includes a control system 106. The monitoring system 102 may be adapted to monitor operation of the drive motor 18 in order to ascertain whether a motor performance parameter 104 is above or below a predetermined value for the motor performance parameter 104. The motor performance parameter 104 may be a motor speed, and the predetermined value may be a minimum speed. The motor parameter 104 may be a motor torque, and the predetermined value may be a maximum torque, for example. In some cases, the motor performance parameter 104 may be an elapsed time value, and the predetermined value may be a maximum elapsed time. For example, a maximum elapsed time may be about 30 minutes, and a maximum torque value may be about 5 inch-ounces.

The monitoring system 102 may be operably coupled to the excitation module 26 so that if the motor performance parameter 104 is out of range, or is approaching a predetermined minimum or maximum value, as the case may be, the monitoring system 102 may instruct the excitation module 26 to create haptic feedback. In some cases, the excitation module 26 may be coupled to the handle 28, so that any vibration caused by the excitation module 26 may be discernible by the user holding the handle 28 when the user is operating the atherectomy system 100. In some cases, the atherectomy system 100 may also include the control system 106 that may be adapted to control operation of the drive motor 18. In some cases, the monitoring system 102 and the control system 104 may be separate. In some cases, the monitoring system 102 may be integrated into the control system 104, creating a combined monitoring and control system 108 (shown in dashed line).

Figure 3:
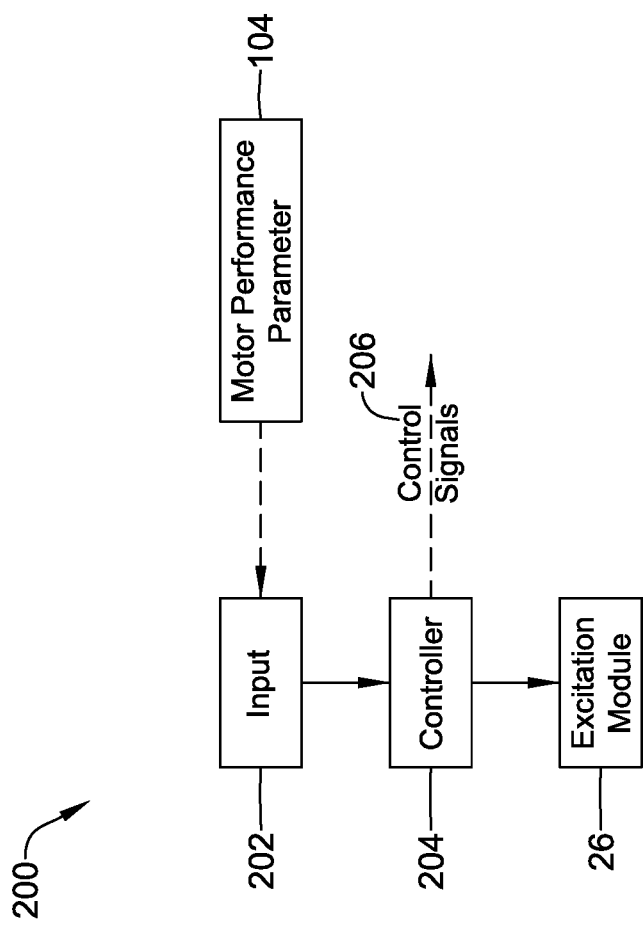
FIG. 3 is a schematic block diagram of an example control system usable with the example atherectomy systems of FIG. 1 and FIG. 3.

FIG. 3 is a schematic block diagram of a control system 200 for an atherectomy system (such as the atherectomy system 10 shown in FIG. 1 or the atherectomy system 100 shown in FIG. 2). In some cases, the control system 200 may be considered as being an example of, or including functionality of, the monitoring module 24 and/or the monitoring system 102), and features of the control system 200 may be combined with features of the monitoring module 24 and/or the monitoring system 102, for example. The control system 200 includes an input 202 that is adapted to receive an indication of the motor performance parameter 104. A controller 204 is operably coupled to the input 202 and to the excitation module 26. In some cases, the controller 204 is adapted to, when the motor performance parameter approaches a limit of a performance range, to activate the excitation module 26 in order to provide haptic feedback to the user that the motor performance parameter is approaching the limit of the performance range. In some cases, the controller 204 may also be adapted to output control signals 206 for operation of a drive motor.

Figure 4:
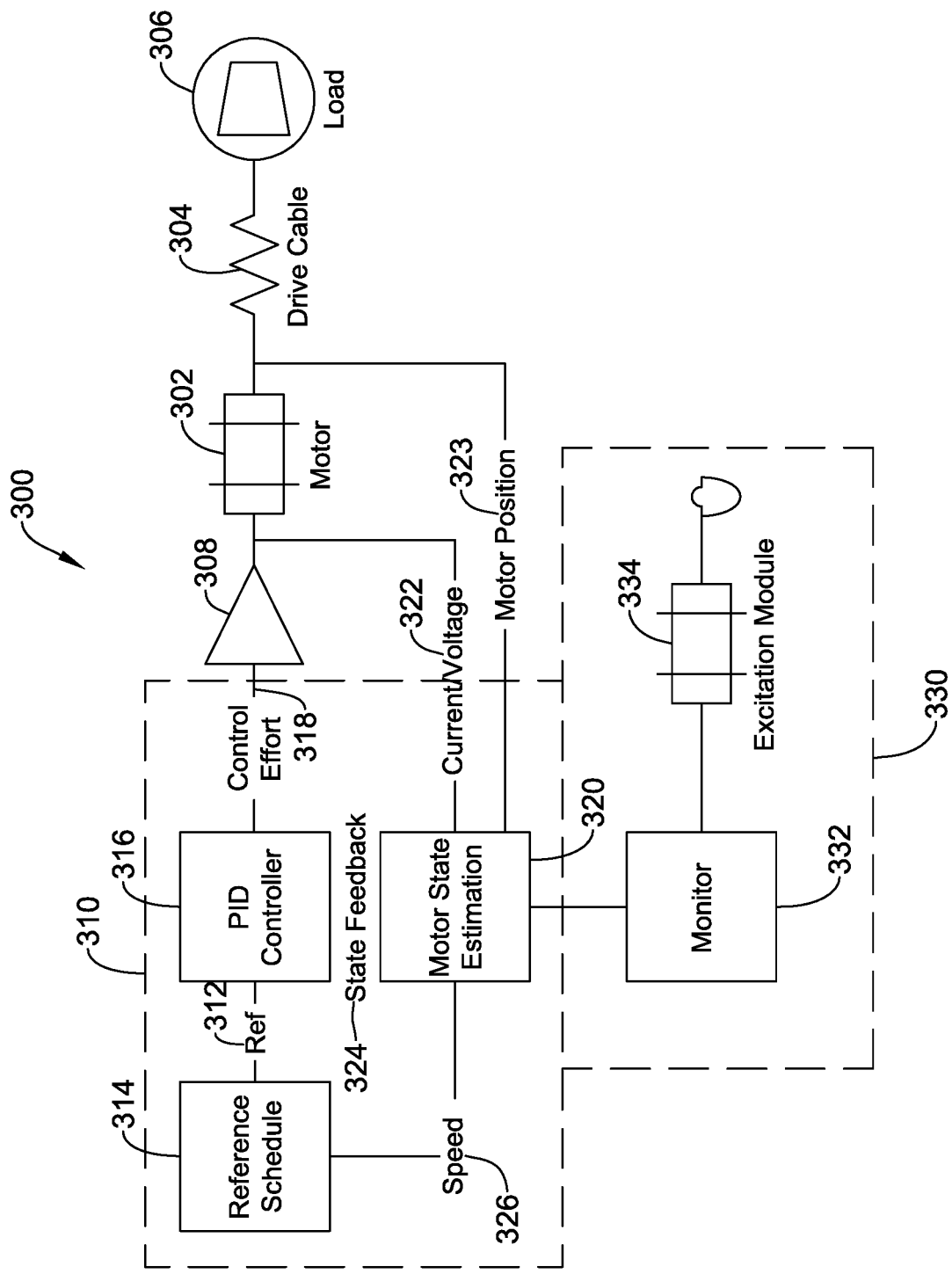
FIG. 4 is a schematic block diagram of an example atherectomy system.

FIG. 4 is a schematic block diagram of an example atherectomy system 300. In some cases, the atherectomy system 300 may be considered as being an example of the atherectomy system 10 (FIG. 1) or the atherectomy system 100 (FIG. 2). In some instances, features of the atherectomy system 300 may be combined with features of the atherectomy system 10 and/or the atherectomy system 100, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the drive module 22 and/or the control system 106, for example.

The drive circuitry 308 receives an input from a feedback portion 310. In some cases, the feedback portion 310 begins with a reference input 312 from a reference schedule block 314, which provides the reference input 312 to a PID controller 316. A PID controller is a controller that includes a (P) proportional portion, an (I) integral portion and a (D) derivative portion. The PID controller 316 outputs a control effort value 318 to the drive circuitry 308. A motor state estimation block 320 receives a current/voltage signal 322 and a motor position signal 323 from the drive circuitry 308 and receives state feedback 324 from the PID controller 316. The motor state estimation block 320 outputs a speed value 326 back to the reference schedule block 314. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed.

In some cases, the atherectomy system 300 also includes a haptic module 330. In some instances, the haptic module includes a monitor block 332 and a excitation module 334. If the monitor block 332 receives from the motor state estimation block 320 an indication that the motor 302 is operating at or near a predetermined limit for motor speed, motor torque and/or elapsed run time, for example, the monitor block 332 activates the excitation module 334. The excitation module 334 causes a vibration that is detectable by the user operating the atherectomy system 300.

Figure 5:
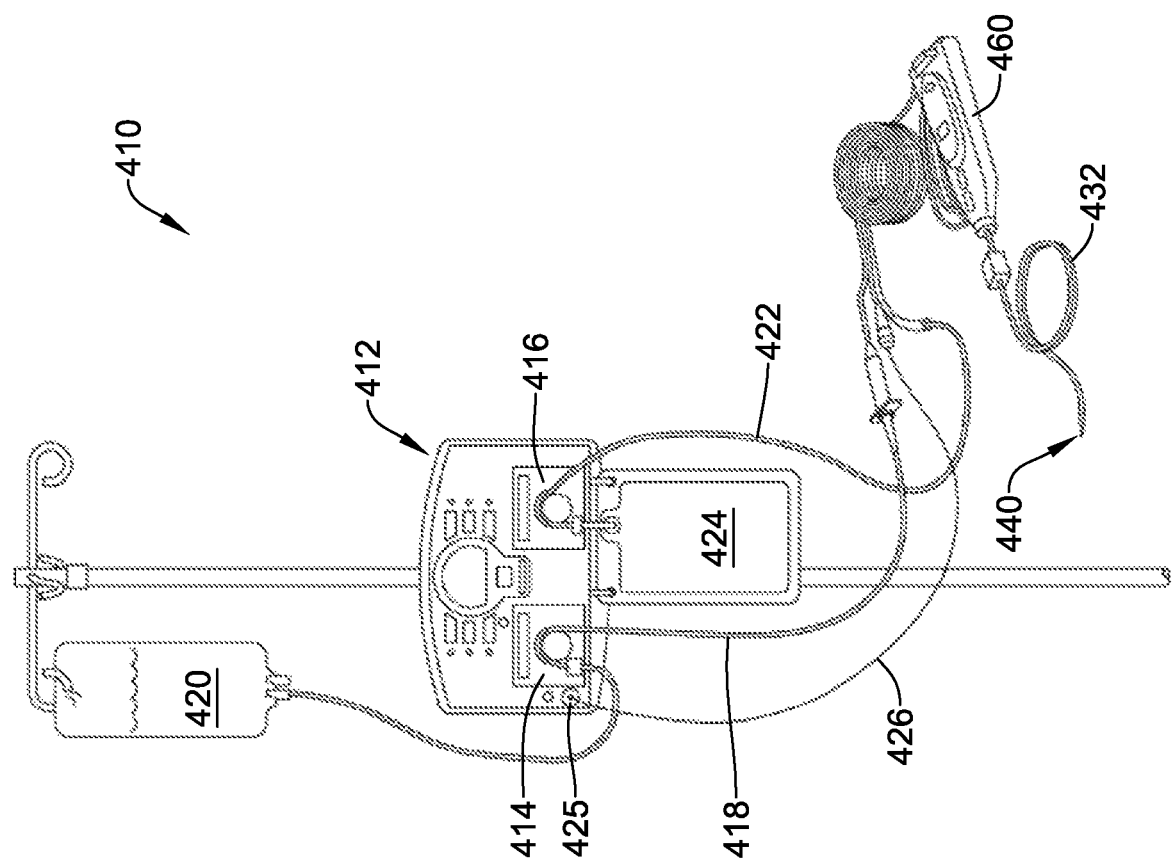
FIG. 5 is a schematic diagram of an example atherectomy system.

FIG. 5 illustrates an exemplary example of an interventional catheter assembly 410 with which the atherectomy systems 10, 100 and 300, the monitoring module 24, the monitoring system 102 and the control system 200 described therein, may be used. The interventional catheter assembly 410 includes a console unit 412, a controller 460, and a catheter system 432 having an operating head 440 located at or in proximity to the distal end of the catheter system. The controller 460 may be used to manipulate (e.g. advance and/or rotate) the catheter system 432 and operating head 440, or alternative controls may be provided. It will be appreciated that at least some of the functionality of the controller 460 and/or the console unit 412 may instead be incorporated into the atherectomy systems 10, 100, 300.

The console unit 412 incorporates an infusion pump 414 and an aspiration pump 416. During operation of the interventional catheter, an infusate conduit 418 draws fluid from an infusate reservoir 420 and operably contacts the infusion pump 414 to provide fluid through an infusion lumen in catheter system 432 to one or more infusion ports provided in proximity to the operating head. Similarly but in reverse, fluids with entrained particulates are withdrawn from the site of intervention through an aspiration lumen in the catheter system 432 and conveyed to an aspiration conduit 422, which is in operable contact with the aspiration pump 416, and communicates with the aspirate collection vessel 424. The console unit 412 may also provide a power source for operating the operating head and system components, or it may be in communication with an external power source. In some cases, the console unit 412 may provide power to the interventional catheter assembly and the controller 460 via a device power port 425 and power cord 426.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 412. The console unit 412 is generally provided as a reusable assembly and is generally operated outside the sterile field. It may be mountable on a portable stand to facilitate convenient placement during interventions.

One function of the console unit 412 is to provide feedback of system and/or environmental conditions or operating parameters. The console unit may output operational information concerning operating conditions and feedback from the material removal site to the operator. In some cases, the console unit 412 may provide continuously updated output to an operator of operating parameters such as operating head rotation rate, which may include the actual run speed as well as the desired speed; operating head advance rate; aspiration rate and/or volume; infusion rate and/or volume; length of the body or matter to be removed that is traversed; and the like.

Certain automated and selectable control features may be implemented in the console unit 412. Preset routines or programs involving various operating parameters may be preselected, stored and selectable by an operator, for example. Thus, in some cases, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as: cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

In some cases, aspiration may be provided. In certain cases, fluid and associated particulates are aspirated from the intervention site at rates of at least 5 ml/min and, in many cases, fluid and associated particulates are aspirated at rates of at least 15 ml/min or at least 25 ml/min. In exemplary interventional catheter systems, the aspiration site may be more than a meter away from the controller 460 through an aspirate removal passageway located within the catheter system 432 and having a diameter of less than 0.10 inch, for example between about 0.050 to 0.070 inch. The distance that the aspirate travels between controller 460 and console unit 412 may be from about ½ meter to several meters, through an aspirate conduit that is between about 0.015 to about 1.0 inch in diameter. The blood and debris being aspirated are relatively viscous fluids, and achieving a relatively constant and high level of aspiration under these conditions is essential.

In one case, aspiration pump 416 may be a multi-lobed roller pump. The rotation rates of multiple rollers, or of a multi-lobed rotating structure, may be variable or selectable to control the aspiration rate and volume. Roller pumps permit fluid to flow in a conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. For example, a collection bag 424 and a sealed aspiration conduit may be provided as part of a sterile disposable interventional catheter kit. A distal end of the aspiration conduit may be pre-mounted on and sealed to the controller 460. A proximal portion of the aspiration conduit is mounted on the aspiration pump prior to operation of the interventional catheter and the aspirate collection bag is mounted to or in proximity to the control module.

The infusion pump 414 may also be a multi-lobed roller pump employing variable or selectable rotation rates to control the infusion rate and volume. A simple bag or another infusate reservoir, such as those used for intravenous infusions, may be used to supply the infusate. For example, an infusate reservoir 420 having a sealed conduit that is mounted in the infusion pump 416 during operation of the interventional catheter may be provided. In some cases, the sealed infusate conduit may be provided as part of the sterile disposable interventional catheter system and a distal end of the infusate conduit may be pre-mounted on and sealed to the controller 460. A proximal portion of the infusate conduit may be connected to an infusate reservoir, such as a saline bag, and mounted in proximity to the infusion pump prior to operation. A control feature that automatically disables the infusion pump and/or power to the operating head may be activated upon detection of a fault (e.g. a bubble) in the infusate conduit.

The console unit 412 may also have control switches for activating and shutting down the aspiration pump and system, and for activating and shutting down the infusion pump and system. These control features may be provided as simple on/off switches. Alternatively, systems providing different levels or rates of aspiration and/or infusion that are selectable by an operator may be provided. In addition, the console unit 412 may be provided with a timing mechanism that determines, and displays, the elapsed time of operation of the operating head and/or the aspiration and infusion systems. The volumes of aspirate withdrawn and the volume of infusate introduced may also be detected and displayed by the console unit 412. Detection systems for monitoring the levels of aspirate and infusate in the respective reservoirs may be incorporated and alarms indicating an overfill condition for the aspirate collection system or a low supply condition for the infusate reservoir may be provided. Backup aspirate collection and infusate supply systems may also be provided.

In some cases, the console unit 412, together with the aspiration pump 416, the infusion pump 414 and the associated control and display features, may be provided as a separate, re-usable unit, that may be used as standard equipment in operating rooms, for example. In the system illustrated, the console unit 412 is not contaminated by contact with blood or aspirate during operation, and the power and control systems are durable and long-lasting and may be reused for many interventions. The console unit 412 may be provided in a housing designed to sit on a platform during operation, or the housing may be designed for mounting on a portable structure, such as an i.v. pole or another structure, or may be a self-contained free-standing portable structure The interventional catheter system, including the catheter system 432 with the operating head 440, the controller 460, the aspirate conduit 422, the aspirate collection vessel 424, and the infusate conduit 418 may be provided as a sterile, single use system kit.

The controller 460, which may be constructed from a durable, sterilizable material, such as hard plastic, may be provided in any convenient ergonomic design and constructed for placement in proximity to and/or in contact with the external body. In one instance, the controller may include an integrated handle for operator convenience in holding and supporting the controller during operation. The catheter system 432, exiting the controller 460, may be axially translatable with respect to the controller 460 as the operating head and catheter system are guided to a target material removal site. It will be appreciated that some of the control and operational features described herein with reference to the controller 460 may be provided in the console unit 412 and, likewise, some of the control and operational features described with reference to the console unit 412 may be provided in the controller 460.

Figure 6:
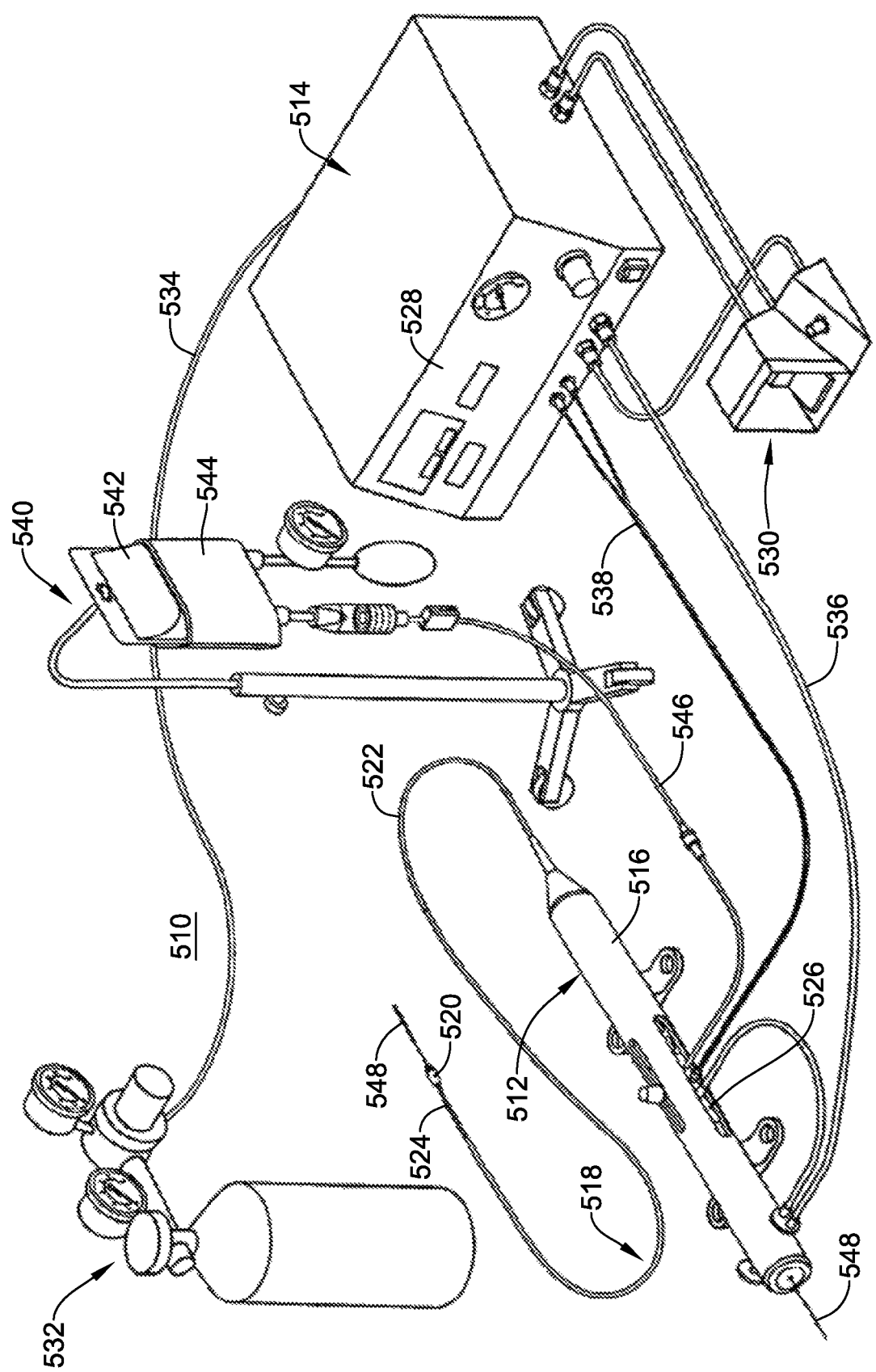
FIG. 6 is a schematic diagram of an example atherectomy system.

FIG. 6 shows an example rotational atherectomy system 510 with which the atherectomy systems 10, 100 and 300, the monitoring module 24, the monitoring system 102 and the control system 200 described therein, may be used. The rotational atherectomy system 510 may include a rotational atherectomy device 512 and a controller 514 for controlling the rotational atherectomy device 512. The rotational atherectomy device 512 may include a housing 516 and an elongate shaft 518 extending distally from the housing 516 to a cutting member 520 located at a distal end of the elongate shaft 518. The elongate shaft 518 may include a drive shaft 524 to provide rotational motion to the cutting member 520. In some instances, the elongate shaft 518 may include an outer tubular member 522 having a lumen extending therethrough and the drive shaft 524 may extend through the lumen of the outer tubular member 522. The drive shaft 524, which may be fixed to the cutting member 520, may be rotatable relative to the outer tubular member 522 to rotate the cutting member 520. In some instances the axial position of the cutting member 520 relative to the outer tubular member 522 may be adjusted by moving the drive shaft 524 longitudinally relative to the outer tubular member 522. For example, the atherectomy device 512 may include an advancer assembly 526 positioned in the housing 516, or otherwise provided with the housing 516, that is longitudinally movable relative to the housing 516. The outer tubular member 522 may be coupled to the housing 516 while the drive shaft 524 may be coupled to the advancer assembly 526. Accordingly, the drive shaft 524 (and thus the cutting member 520) may be longitudinally movable relative to the outer tubular member 522 by actuating the advancer assembly 526 relative to the housing 516.

The rotational atherectomy device 512 may include a prime mover (not shown) to provide rotational motion to the drive shaft 524 to rotate the cutting member 520. For example, in some instances the prime mover may be a fluid turbine within the housing 516, such as provided with the advancer assembly 526. In other instances, however, the prime mover may be an electrical motor, or the like. The controller 514 may be used to control the prime mover. For example, the user may provide power to the prime mover and/or control the speed of rotation of the drive shaft 524 via the controller 514. For example, the front panel 528 of the controller 514 may include a user interface including a power switch, speed control mechanism (e.g., a speed control knob and/or buttons), a display, and/or other features for controlling the rotational atherectomy device 512. In some instances, the rotational atherectomy system 510 may include a remote control device 530, such as a foot pedal, a hand control, or other mechanism which may be used to control the power and/or speed to the prime mover, for example.

In instances in which the prime mover is a turbine, the rotational atherectomy system 510 may also include a pressurized fluid source 532 providing a pressurized fluid to the turbine to rotate the drive shaft 524. In some instances, as shown, the pressurized fluid source 532 may be a tank of pressurized fluid (e.g., compressed air), which may or may not include an air compressor. In other instances, the pressured fluid source 532 may be provided external of the rotational atherectomy system 510, such as from a wall outlet at the medical facility. The pressured fluid source 532 may be coupled to the controller 514 via a fluid conduit 534, which in turn is coupled to the rotational atherectomy device 512 via a fluid conduit 536. The controller 514 may regulate the flow and/or pressure of fluid through the fluid conduit 536 to the rotational atherectomy device 512 to control the speed of rotation of the drive shaft 524 and cutting member 520, for instance.

In instances in which the prime mover is an electric motor, the electric motor may be coupled to the controller 514 via an electrical connection to control the electric motor and/or provide electricity to the electric motor.

In some instances, the rotational atherectomy device 512 may include a speed sensor, such as an optical speed sensor, coupled to the controller 514 via a connector 538, such as a fiber optic connector to provide speed data to the controller 514. In other instances, an electronic sensor, such as a Hall Effect sensor, or other type of sensor may be used to sense the speed of the drive shaft 524 and cutting member 520. The speed data may be displayed, such as on the front panel 528 and/or the controller 514, and/or used to control the speed of the cutting member 520, such as maintaining a desired speed of the cutting member 520 during a medical procedure.

In some instances, the rotational atherectomy system 510 may be configured to infuse fluid through the elongate shaft 518 to the treatment site and/or aspirate fluid through the elongate shaft 518 from the treatment site. For example, the rotational atherectomy system 510 may include a fluid supply 540 for providing a flow of fluid through a lumen of the elongate shaft 518 to a treatment site. In some instances the fluid supply 540 may include a saline bag 542 which may be pressurized by a pressure cuff 544 to provide a pressurized fluid (e.g., saline) to the rotational atherectomy device 512 through a fluid supply line 546. In other instances, an infusion pump, such as a peristaltic pump, may be used to deliver pressurized fluid to the rotational atherectomy device 512. Additionally or alternatively, in some cases the rotational atherectomy system 510 may be configured to aspirate fluid from the treatment site. For example, the rotational atherectomy system 510 may include an aspiration pump, such as a peristaltic pump, to generate a vacuum to aspirate fluid through a lumen of the elongate shaft 518 to a fluid collection container (not shown), if desired.

In some instances, the elongate shaft 518 of the rotational atherectomy device 512 may be advanced over a guidewire 548 to a treatment site. For example, the drive shaft 524 may include a guidewire lumen through which the guidewire 548 may pass. Additionally or alternatively, the elongate shaft 518 may be advanced through a lumen of a guide catheter to a treatment site.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy system, comprising:
a drive mechanism including a drive cable and a drive motor adapted to rotatably actuate an atherectomy burr; and
a control system adapted to regulate operation of the drive mechanism, the control system including:
a drive module adapted to provide an operational signal to operate the drive mechanism;
a monitoring module adapted to monitor operation of the drive mechanism and to determine if the drive motor is operating within a predetermined range for each of one or more operating parameters; and
an excitation module operably coupled to the drive mechanism and adapted to provide haptic feedback to a user of the drive mechanism if the monitoring module determines that the drive motor is not operating within the predetermined range of each of the one or more operating parameters.

2. The atherectomy system of claim 1, wherein one of the one or more operating parameters comprises.

3. The atherectomy system of claim 1, wherein one of the one or more operating parameters comprises.

4. The atherectomy system of claim 1, wherein one of the one or more operating parameters comprises.

5. The atherectomy system of claim 1, wherein the drive mechanism further comprises a handle with the drive cable extending through the handle, and the excitation module, when actuated, causes a detectable vibration within the handle.

6. The atherectomy system of claim 1, wherein the excitation module comprises a vibrator motor that, when actuated, causes a detectable vibration within the drive mechanism.

7. The atherectomy system of claim 1, wherein when the monitoring module determines that the drive motor is operating outside the predetermined range by a preset amount, the excitation module is further adapted to increase the haptic feedback.

8. An atherectomy system, comprising:
a handle;
a drive motor adapted to rotate a drive cable extending through the handle and operably coupled to an atherectomy burr;
an excitation module operably coupled to the handle and adapted to provide haptic feedback to a user of the atherectomy system; and
a monitoring system adapted to monitor operation of the drive motor, the monitoring system further adapted to:
monitor a drive motor performance parameter; and
when the drive motor performance parameter approaches a predetermined value for the drive motor performance parameter, actuate the excitation module in order to provide haptic feedback to the user of the atherectomy system that the drive motor performance parameter is approaching the predetermined value for the drive motor performance parameter.

9. The atherectomy system of claim 8, further comprising a control system adapted to control operation of the drive motor.

10. The atherectomy system of claim 9, wherein the monitoring system is integrated into the control system.

11. The atherectomy system of claim 8, wherein the motor performance parameter comprises a motor speed.

12. The atherectomy system of claim 8, wherein the motor performance parameter comprises a motor torque.

13. The atherectomy system of claim 8, wherein the motor performance parameter comprises an elapsed run time.

14. The atherectomy system of claim 8, wherein the haptic feedback comprises a detectable vibration.

15. A control system for an atherectomy system including a drive motor adapted to rotate a drive cable operably coupled to an atherectomy burr, the control system comprising:
an input adapted to receive an indication of a drive motor performance parameter;

an excitation module adapted to provide haptic feedback to a user of the atherectomy system a controller operably coupled to the input and to the excitation module, the controller adapted to, when the drive motor drive performance parameter approaches a limit of a performance range, to activate the excitation module in order to provide haptic feedback to the user that the drive motor performance parameter is approaching the limit of the performance range.

16. The control system of claim 15, wherein the controller is further adapted to output control signals for operation of the drive motor.

17. The control system of claim 15, wherein the drive motor performance parameter comprises a motor speed.

18. The atherectomy system of claim 15, wherein the drive motor performance parameter comprises a motor torque.

19. The atherectomy system of claim 15, wherein the drive motor performance parameter comprises an elapsed run time.

* * * * *